United States Patent [19]

Germaske

[11] Patent Number: Plant 5,688

[45] Date of Patent: Mar. 11, 1986

[54] ORCHID-SLC, HAZEL BOYD, VARIETY JOHN GERMASKE

[76] Inventor: John Germaske, 9395 SW. 77 Ave., Miami, Fla. 33156

[21] Appl. No.: 643,634

[22] Filed: Aug. 23, 1984

[51] Int. Cl.[4] ..... A01H 5/00
[52] U.S. Cl. ..... Plt./68
[58] Field of Search ..... Plt./68

*Primary Examiner*—Robert E. Bagwill

[57] ABSTRACT

A new and distinct variety of orchard hybrid plant which is outstanding and distinct from other orchids because of its matchless superior flowers, which combine the rare brilliant red coloring of the petals, the backside of the sepals turning to orange color at maturity, long lasting quality, extra large size of the petals for this type of plant, and vigorous and reliable blooming, the new variety is also distinctive from its parent population and similar hybrids by its plant structure.

2 Drawing Figures

DISCOVERY OF THE NEW VARIETY

This new orchard plant originated as a seedling from the following unpatented varieties:

Sophrolaeliocattleya Jewel Box, variety "Beverly", female parent, and Sophrolaeliocattleya California Apricot, variety "Orange Circle", male parent.

The orchid plant, resulting from the cross, was developed by Rod McLellan Company, 1450 El Camino Real, South San Francisco, Calif., and was named by the undersigned "Sophrolaeliocattleya SLC Hazel Boyd", which name was registered with The Royal Horticultural Society, London, England, on Mar. 4, 1975.

The new orchid plant of the application was discovered in 1979 by the undersigned and immediately recognized as distinctive and superior in its flowers and an outstanding member of a large population of over six hundred (600) plants produced from the above described cross. The varietal name "John Germaske" was added to the Hybrid's name to identify the new variety of this application.

ASEXUAL REPRODUCTION

After the discovery of this new variety with its distinct and outstanding characteristics, the original plant was placed in my Orchard Nursery in Miami, Fla. During the years following its discovery, the plant was asexually reproduced by me through botanical divison. All of the propagations thus produced since this plant was discovered in 1979 have been identical to the mother plant in all general and specific characteristics, and all continued to be readily distinguishable from both parent plants and other plants in the same general population.

DESCRIPTION OF THE PHOTOGRAPHS

DESCRIPTION OF THE FLOWER

The flowers of the new variety SLC, "John Germaske" are of exceptional outstanding red coloring. As the flower attains maturity, the back side of the sepal becomes orange in color. In the following description, the principal colors are specified by reference to the code numbers of The Royal Horticultural Society Colour Charts (hereinafter HCC) and The British Colour Council Dictionary of Color Standards (hereinafter BCC).

When the flower initially opens the petals and sepals are Current Red (HCC 820/2), as it matures it lightens to Post Office Red (BCC 209). The lateral sepals have faint Indian Orange (713) stripes running laterally. The outer edge of the lip is Current Red (HCC 820/2) lightening to center with golden veins. The base of the petals and sepals are pale Indian Orange (HCC 713). The reverse side of the sepals turn to Indian Orange (HCC 713) at maturity.

The flowers are of long lasting quality, remaining in good form up to two months and even longer in colder climates. This is a longer flowering period than that of the parent population and other similar orchids.

The petals are extra large size for this type of plant. The flowers of this new variety are of the following average dimensions:

Natural spread of the flower: 10.5 cm
Petal width: 5.3 cm
Petal length: 5.7 cm
Dorsal sepal width: 2.5 cm
Dorsal sepal length: 5.8 cm
Lateral sepal width: 2.4 cm
Lateral sepal length: 5.3 cm
Labellum length: 4.0 cm
Labellum width: 2.9 cm

DESCRIPTION OF THE PLANT

Figure 1:
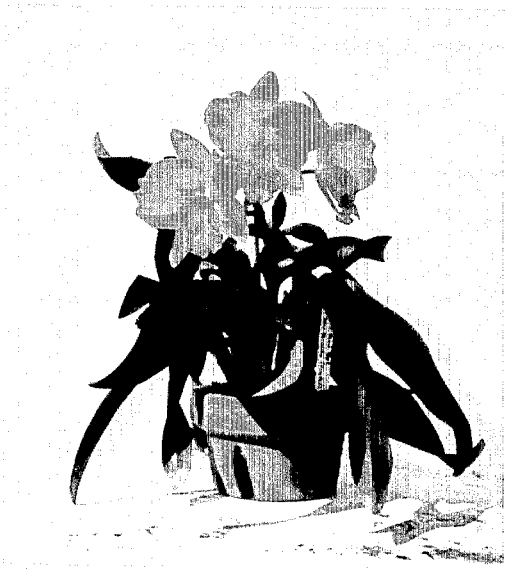
FIG. 1 is a color photograph showing a typical adult plant of this new variety.
Figure 2:
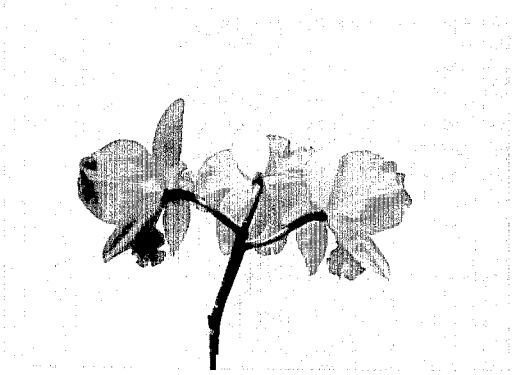
FIG. 2 is a color photograph of the reverse side of the flower showing the coloring of the maturing flower.

The plant is shown in FIG. 1, a color photograph accompaying this specification.

The plant attains a height of 26 cm. to 30 cm. on maturity.

The leaves at full growth reach 19 cm. to 23 cm, and are narrow and semi-upright. As the plant matures, the older leaves droop and become what is commonly referred to as mule-ear type leaves, this is a most desirable feature as the drooping leaves provide for an unobstructed view of the flowers.

The rizone is very short, ranging from non-existent to 0.5 cm.

This plant has been uniformly vigorous in its growth habits, yet quite compact in size. It produces multiple growths with an average of 3 to 4 flowers per stem. This plant will often produce flowers without a sheath.

The plant will reliably flower once and frequently twice each year.

I claim:

1. A new and distinctive variety of orchard plant substantially as herein described and illustrated and distinguished from its parent and other orchids by its combination of matchless rare brilliant red coloring, the color of the back of the sepals turning to orange at maturity, large size of the flowers, superior lasting quality and vigorous reliable blooming.

* * * * *